United States Patent [19]

Acree et al.

[11] Patent Number: 4,567,042

[45] Date of Patent: * Jan. 28, 1986

[54] INACTIVATED CANINE CORONAVIRUS VACCINE

[75] Inventors: William M. Acree; Bobby Edwards, both of Temple, Tex.; John W. Black, Milton, Tenn.

[73] Assignee: American Home Products Corporation, New York, N.Y.

[*] Notice: The portion of the term of this patent subsequent to Jan. 28, 2003 has been disclaimed.

[21] Appl. No.: 618,638

[22] Filed: Jun. 7, 1984

Related U.S. Application Data

[63] Continuation-in-part of Ser. No. 504,434, Jun. 15, 1983.

[51] Int. Cl.$^4$ ............................................. A61K 39/12
[52] U.S. Cl. ..................................................... 424/89
[58] Field of Search ........................... 424/89; 435/235

[56] References Cited

PUBLICATIONS

Gill, Michael A., *Isolation and Characterization of a Canine Coronavirus*, Ph.D Thesis, University of Nebraska-Lincoln, 1982.

Pollock et al., Vet. Clin. North Am., Aug. 1983, 13(3) pp. 551–566.

Appel et al., Canine Practice, vol. 7, No. 4, pp. 22–34 (1980).

*Primary Examiner*—Sidney Marantz
*Assistant Examiner*—Shawn P. Foley
*Attorney, Agent, or Firm*—Adley F. Mandel

[57] ABSTRACT

An efficacious parenterally administered inactivated canine coronavirus vaccine which provides systemic, humoral protection and also protection of the intestinal tract in dogs from infection by virulent canine coronavirus is produced. A method for propagation of the canine coronavirus and its attenuation and a method of evaluating the effectiveness of a canine coronavirus vaccine in canines is also disclosed.

19 Claims, No Drawings

INACTIVATED CANINE CORONAVIRUS VACCINE

This application is a continuation-in-part of application Ser. No. 504,434 filed June 15, 1983, entitled Canine Coronavirus Vaccine. The entire contents of that application are incorporated herein by reference.

The present invention concerns inactivated canine coronavirus vaccine, its method of preparation and adjuvants for use therewith.

More particularly the present invention concerns an inactivated canine coronavirus vaccine which induces both systemic immunity and local immunity in the intestinal tract.

The veterinary community has recognized the need for a canine coronavirus vaccine. The safety of modified live virus vaccines must be proven by the developer and licensed by a United States Government Agency. However, misuse of modified live virus vaccines or use of modified live virus vaccines in a compromised host can lead to field problems. The misuse of product involves, but is not limited to, the combining of several vaccines for simultaneous use when these vaccines have not been studied or recommended for use in this manner. A compromised host includes, but is not limited to, the inoculation of animals undergoing an active infectious process, animals which are in general poor health and animals immunologically incompetent. The immunological incompetence may be present because of immunological deficiency due to inherited genetic traits, because of a concurrent infectious process or treatment with certain chemical compounds, such as dexamethasone.

Some examples of modified live virus vaccines which have been licensed for sale but may have caused post vaccinal problems associated with field misuse or use in compromised host are the Modified Live Low Egg Passage Rabies Vaccine, some Modified Live Canine Distemper Vaccines, a Modified Live Canine Coronavirus Vaccine and a Modified Live High Egg Passage Rabies Vaccine. Improved diagnostic techniques have aided in detecting problems associated with modified live virus vaccines.

Safety problems in the field due to misuse or due to use in a compromised host can be minimized or eliminated with an inactivated virus vaccine. While inactivated or killed virus vaccines are preferable because of safety, they have in the past been of inferior efficacy to modified live virus vaccines. While production techniques and adjuvant systems have brought about the development of some highly effective inactivated viral vaccines, the results due to a particular technique or a particular adjuvant system have been unpredictable.

Inactivated virus vaccines have been developed for the most part in the host ranges of farm animals to the feline. The only currently USDA licensed inactivated products for the canine have been for Canine Parvovirus Enteritis and Rabies. While other inactivated viral products for the canine have been produced they have not met with market acceptance because of inferior effectiveness as compared to corresponding modified live virus vaccines.

A problem in the production of an inactivated canine coronavirus vaccine was the general belief that intestinal protection could not be achieved without vaccine viral replication within the target tissue of the intestinal tract. Viral replication cannot be obtained with an inactivated viral vaccine.

It was expected that an oral-intrasnasal route of vaccination with a live virus vaccine would be required to insure not only the achievement of systemic immunity but also the induction of local immunity in the intestinal tract. Unexpectedly, it has been found that a parenterally administered killed canine coronavirus vaccine induces systemic immunity and also induces local immunity in the intestinal tract.

It is an object of the present invention to provide an inactivated canine coronavirus vaccine which produces both systemic immunity and local immunity in the intestinal tract when administered parenterally.

It is a further object of this invention to provide an inactivated canine coronavirus vaccine which is as effective as the known modified live canine coronavirus vaccine.

It is another object of the present invention to provide a process for inactivating a canine coronavirus and for producing a vaccine therefrom.

It is still another object of the present invention to provide an adjuvant system for an inactivated canine coronavirus vaccine so that its effectiveness is equal to that of a modified live canine coronavirus vaccine.

SUMMARY OF THE INVENTION

A major aspect of this invention is the use of an inactivated canine coronavirus vaccine in the prevention of the canine coronaviral disease complex. Other aspects of this invention involve the composition of the canine coronavirus (CCV) vaccine, the inactivation process used with the canine coronavirus and the adjuvants used in conjunction with the CCV vaccine Isolates of Canine Coronavirus such as the I-171 strain (ATCC VR-809), the TN-449 (ATCC VR-2068) or any of three canine coronaviruses available from Cornell University (K378-8, S378-6 and A76 strains) may be used for manufacturing an inactivated CCV vaccine. The inactivated CCV vaccine composition includes one or more isolates of an inactivated canine coronavirus having pre-inactivation virus titers of greater than 4.0 logs of virus particles/ml. (or dose) and preferably greater than 5.0 logs of virus particles/ml. (or dose) as measured by the $FAID_{50}$ (Fluorescent Antibody Infectious Dose) method (King et al, Can. Journal of Comparative Medicine and Vet Science 29 pp 85–89, 1965). The typical dose amount is one milliliter.

Inactivated CCV fluids may also be concentrated by any number of available techniques such as an Amicon concentrating device, Pellicon (Millipore) concentration device, precipitation techniques, such as ammonium chloride, concentration with Carbowax liquid or wax in conjunction with dialysis tubing, or adjuvant concentration techniques, such as with aluminum phosphate.

Titers as high as 5 to 7 logs $FAID_{50}$ have been obtained. The inactivated CCV vaccine composition includes one or more inactivated canine coronaviruses and also may contain an attenuated modified live or killed canine parvovirus (CPV). In addition, the vaccine may contain in any combination or singularly, additional attenuated modified live viruses or killed viruses such as Canine Distemper virus, Canine Parainfluenza virus, Canine Adenovirus I, Canine Adenovirus II, Canine Rotavirus, Measles virus, Canine Calicivirus and Canine Herpesvirus. The inactivated CCV vaccine produces a complete immunological response to the virus infection.

In one embodiment, this invention relates to a canine coronavirus vaccine composition comprising an amount of inactivated canine coronavirus which is equivalent to a virus titer of from about 4 to 7 logs $FAID_{50}$ per milliliter, in an aqueous solution having a pH between about 6.8 and 7.8.

The vaccine composition comprises a sufficient amount of the canine corona-virus antigen to produce an immunological response in a dog and a nontoxic pharmaceutically acceptable adjuvant or adjuvant combination.

The method for propagating the CCV in mammalian cells includes the steps of inoculating mammalian tissue culture cells with CCV, cultivating the cells into a one hundred percent (100%) confluent tight monolayer before said inoculating step or within 24 hours of said inoculating step, harvesting the cells between 24 and 96 hours after inoculation and collecting the propagated virus from the harvested cells.

The mammalian tissue culture cells are inoculated with CCV at a CCV virus (measured by the $FAID_{50}$ method) to cell ratio of 1:500 to 1:1, preferably 1:100 to 1:5, more preferably 1:75 to 1:10. The mammalian tissue culture cells include but are not limited to Crandall Feline Kidney Cells (CRFK), Wood's Feline Cell Line (FC), a Dog Kidney Cell Line (DK), Madin Darby Canine Kidney (MDCK) and the canine A72 cell line. The CCV is added to a suspension of the cells or is applied to a monolayer of the cells. The amount of cells and virus should be such that a confluent tight monolayer of the cells will form within 12–48, preferably 24–36, hours after inoculation. Optimally, at the time of inoculation the cells should be present in the growth vessel in an amount sufficient to form a monolayer of cells of at least 100,000 to 1,000,000 cells per square centimeter ($cm^2$) within about 12–48 hours after inoculation, preferably within 24 hours after inoculation. However a lesser number of cells may be used. Preferably the cells are present in an amount sufficient to form between 150,000 to 500,000 cells/$cm^2$ within 12–48 hours, preferably within 24 hours. The virus is absorbed on the cells for at least 60 minutes but usually less than 300 minutes, preferably between 90 and 240 minutes at 28° to 40° C., preferably 35° to 38° C.

Harvestable virus titers of at least about 1,000 particles and usually at least about 2,000 particles as measured by the $FAID_{50}$ method can be obtained within 18 hours after inoculation, however, in some circumstances it may take up to 120 hours or longer to obtain maximum virus titers. Maximum virus titers are usually obtained within about 24 to 96 hours after inoculation. The cell monolayer is removed either by freeze-thawing or by enzymatic action to increase the viral content of the harvested fluids. The harvested fluids are then either inactivated or stored frozen.

A further aspect of the invention concerns the route of administration. The induction of humoral-systemic protection as measured by serum neutralizing antibody levels as well as the induction of local immunity in the intestinal tract is an important feature of this invention. The oral-intranasal routes of administration should elicit both types of protection. However, the general marketplace acceptance of this route of administration in not good and, therefore, the use and subsequent protection afforded by a CCV vaccine would not be realized. A USDA licensed modified live virus vaccine, described in patent application Ser. No. 504,434, supra, which is parenterally administered will also provide humoral and localized immunity. Therefore, one major aspect of this invention is the parenteral vaccination with an inactivated CCV vaccine which induces both humoral immunity and localized immunity. The term parenteral vaccination is intended to include subcutaneous and intramuscular inoculation routes.

In still another aspect, the invention relates to a method of protecting dogs against virulent canine coronavirus comprising inoculating a dog with inactivated canine coronavirus vaccine prepared by a process which comprises the steps of growing a strain of canine coronavirus in a non-oncogenic cell culture and then inactivating the virus. In a still a further embodiment this invention relates to a method of protecting dogs from meningeal infection due to coronavirus which comprises parenterally inoculating the animal with a killed, adjuvanted coronavirus vaccine.

The vaccine is preferably parenterally administered in a dose of at least 10,000 inactivated virus particles (4 logs of virus particles) per dose, preferably at least 5.0 logs of virus particles per dose. The vaccine may be administered in either a one or two dose regimen. The second dose should be no more than six weeks after the first. Preferably the second dose is administered two to three weeks after the first dose.

Another aspect of this invention is the inactivation of the Canine Coronavirus. CCV fluids can be inactivated with a number of inactivating agents such as, but not limited to, binary ethyleneimine, acetyl ethyleneimine, beta-propriolactone, formalin, phenol, ultraviolet radiation or gamma irradiation.

Beta-propriolactone at concentrations of 0.01 to 0.5% are preferably used. Concentrations of beta-propriolactone of 0.5% to 0.2% being most frequently used. The inactivating agent is added to virus fluids contained in the propagating vessels, fluids which have been harvested from the propagating vessel and combined or virus fluids which have been harvested from the propagating vessels, combined, stored frozen and then thawed.

Beta-propriolactone is added to the virus fluids, with the adverse shift in pH to acidity being controlled with sodium hydroxide or sodium bicarbonate solution. The combined inactivating agent-virus fluids are incubated at temperatures from 4° C. to 37° C. Incubation times of 24 to 72 hours are used.

Another inactivant used is binary ethyleneimine. Equal volumes of a 0.2 molar bromoethylamine hydrobromide solution and a 0.4 molar sodium hydroxide solution are mixed and incubated at about 37° C. for 60 minutes. The resulting cyclized inactivant is binary ethyleneimine, which is added to the virus fluids at 0.5 to 4 percent, volume to volume. The inactivating virus fluids are held from about 4°–37° C. for 24 to 72 hours with periodic agitation.

Another aspect of this invention is the adjuvant system. Individual or combinations of various adjuvants may be utilized to inhance the immune response. Adjuvants such as, but not limited to, aluminum phosphate, ethylene maleic anhydride, Neocryl A640, and aluminum hydroxide may be utilized. Neocryl is a trade name for a latex emulsion of a copolymer of styrene and a mixture of acrylic acid and methacrylic acid. Neocryl A640 is an uncoalesced aqueous acrylic copolymer with styrene, having pH 7.5, viscosity 100 cps (Brookfield 25° C.), weight per gallon is 8.6 pounds as supplied containing 40 percent solids by weight and 38 percent solids by volume. The numeral A640 denotes a grade thereof. Other useful Neocryl grades are 520,625, and 966. The term "CSMA" will be used hereinafter to refer to a copolymer of styrene and a mixture of acrylic acid and methacrylic acid.

Ethylene maleic anhydride (EMA) prepared at a 5 percent weight/per vol. concentration in water is added to the inactivated virus fluids at 0.01 percent to 6 percent volume to volume concentration. The pH of the resulting fluids is adjusted to 7.1 to 7.7 by addition of 1 normal sodium hydroxide.

CSMA prepared in a 50 percent volume per volume suspension in water is added to the inactivated CCV fluids from 0.1 percent to 10 percent volume. Usually there is no need for a pH adjustment as the CSMA is of a neutral pH.

Combining of two or more adjuvants may be accomplished as in the following, but are not limited to this combination. Ethylene maleic anhydride as described is added at 0.01 percent to 6 percent volume to volume to the inactivated virus fluids. The mixture is adjusted to a 7.1 to 7.7 pH by addition of 1 normal sodium hydroxide. The addition of 0.01 percent to 10 percent of the CSMA, as described, is accomplished with no further pH adjustments being required.

Thus is a further aspect the invention comprises a veterinary vaccine composition comprising an antigen, a pharmaceutically acceptable carrier, and an adjuvant which is at least one member selected from the class consisting of ethylene maleic anhydride and a copolymer of styrene with a mixture of acrylic acid and methacrylic acid.

Another major discovery of this invention is that, unexpectedly, the inactivated virus vaccine will provide localized intestinal protection as measured by vaccination-challenge studies when the vaccine is administered parenterally as well as expected humoral, systemic protection as measured by serum neutralizing antibody levels. Induction of localized immunity has been associated with routes of vaccination other than parenteral and the possibility of providing local immunity to the intestinal tract by parenteral vaccination with CCV was deemed unlikely, especially with a killed antigen. The systemic immunity is likely due primarily to the presence of gamma-immunoglobulin (IgG) and the local immunity in the intestinal tract is likely due at least partially to the presence of alpha-immunoglobulin (IgA) as well as IgG. The presence of IgA is not expected with a killed vaccine.

Vaccinated dogs, given one dose of killed CCV vaccine, when challenged, indicated a reduction of up to 95 percent in intestinal infection as compared to unvaccinated controls. The data thus supports the uniqueness of this portion of the discovery that parenterally administered inactivated CCV vaccine provides systemic, humoral protection as well as local immunity in the intestinal tract.

Another feature of this invention comprises the means by which the vaccine is evaluated in canines. The vaccine is designed to prevent systemic and localized gastroenteritis infections induced by the CCV.

Circulating or humoral antibody evaluations were conducted on blood samples taken 14 and 21 days after parenteral vaccination with a 1 ml. dose of vaccine per dog. At 21 days after vaccination, vaccinated and non-vaccinated dogs were intranasally-orally challenged with virulent canine coronavirus. The onset of disease is rapid and sudden. Disease symptoms are seen as early as 24 hours after challenge in susceptible dogs. The duration of symptoms is usually 24–96 hours, but can extend to 10 days. In evaluating the effectiveness of the vaccine, the animals are euthanized at 5 days after challenge. The intestinal tract from the pyloric valve to the large intestine is removed. The intestines are processed and examined by impression smear scrapings or exfoliated intestinal epithelium is used.

The impression smears are made by scraping the epithelial lining systematically at several locations throughout the intestine. The scrapings are put on slides and processed for direct fluoroscent antibody staining to detect CCV infected cells. The same epithelial scrapings may be exfoliated by placing the scrapings in phosphate buffered saline. The epithelium saline mixture is agitated to suspend the individual cells in the saline. Then, samples of the suspensions are placed on slides to be processed for direct fluoroscent antibody (FA) staining for CCV.

The examination of the slides reveals the extent of specific fluorescence as a measure of virus infection. The degree of fluorescence based on the number of infected cells per field in conjunction with the number of samples examined per dog yield a numerical value of infection which can be assigned to each individual animal. Thus, evaluation as to degree or extent of CCV infection in the intestinal tract is obtained. Comparison of the values from vaccinated and non-vaccinated dogs yields a means of evaluating the effectiveness of the vaccine in preventing intestinal infection.

One process of making a canine corovavirus vaccine according to this invention comprises the steps of:

a. inoculating a suspension of mammalian tissue cell cultures with canine coronavirus;
b. harvesting said cells after about 24 to 96 hours; and
c. collecting the propagated virus from the harvested cells;
d. inactivating the propagated virus; and
e. adding an adjuvant to the inactivated composition.

In order more clearly to disclose the nature of the present invention, specific examples of the practice of the invention are hereinafter given. It should be understood, however, that this is done solely by way of example and is intended neither to delineate the scope of the invention nor limit the ambit of the appended claims. In the examples, all temperatures are stated in degrees centigrade, logs means logs to the base 10, and the following abbreviations are used: "g." for grams, "mcg." for micrograms, "ml." for milliliters, "min." for minutes, and "hr." for hours.

EXAMPLE 1

This example illustrates vaccine production.

The production strain was orginally isolated from a dog which had died of CCV enteritis. The virus was serially propagated in Crandall Feline Kidney Tissue (CRFK) culture. Upon receipt the virus was designated CCV-MSV and passaged once to Master Seed CCV-MSV(X). The CCV-MSV (Canine Corona Virus-Master Seed Virus) culture has been deposited with the American Type Culture Collection in Rockville, Md. and given ATCC Deposit No. VR 2068. In vaccine production the cell cultures were grown in dynamic cultures. In some preliminary runs, static cultures were used. Cell cultures were grown in minimal essential media (MEM) supplemented with vitamins, non-essential amino acids, sodium pyruvate, sodium bicarbonate and L-glutamine. The amount of 30 mcg/ml. of gentamicin was added as a preservative. A 5-10 percent by weight concentration of bovine serum was added for cell growth. The serum concentration was reduced to not greater than 1 percent for a maintenance medium. Trypsin was added at a concentration of 0.5 ml./liter of medium to promote virus infectivity.

Confluent cultures of CRFK cells were trypsinized and planted into roller cultures so that a density of 150,000 cells per $cm^2$ was obtained after 24 hours. Cultures were grown at 28° to 40° C., preferably 35°–38° C. The growth media was removed.

The production seed virus was thawed in cool running water. Sufficient virus was added to achieve a minimum multiplicity of infection (MOI) ratio of 1:100. A 2000 $cm^2$ bottle contained 300–500 million cells. At a 1:50 MOI $300\times10^6$ divided by 50 yielded a minimal infective virus inoculum of $6\times10^6$ or $10^{6.8}$ $FAID_{50}$ per roller. Virus seeds and product harvests yielded $10^{5.5}$ to $10^{7.0}$ $FAID_{50}$ per ml. Thus 20 ml. of undiluted to 1 ml. of undiluted seed was usually used per bottle. The seed was brought up to a volume of 50 ml. per roller bottle with culture medium. The virus was allowed to adsorb on monolayers or in suspension for 2 hours at 35° to 38° C.

A specific example used a seed titered at $10^{5.7}$ $FAID_{50}$ per ml. with 15 ml. per roller used as the inoculum. Thirty two roller bottles were inoculated as described. The bottles were refed with 2 liters of MEM at 1 percent FCS and 0.5 ml. of trypsin. The fluids were harvested along with the cellular material 48 hours after infection, dispensed and frozen at −40° C. or lower.

The bottles yielded 66.5 liters of virus fluids. The titer of the fluids was $10^{5.0}$ $FAID_{50s}$ per ml.

EXAMPLE 2

This example illustrates an inactivation procedure.

Non-frozen canine coronavirus fluids produced as described in Example 1 were inactivated by binary ethyleneimine inactivation (BEI). Stock Solution A of 0.2 molar bromoethylamine hydrobromide was prepared by adding 40.98 grams to deionized water and made up to 1000 ml. Solution B was sodium hydroxide, 0.4 molar. This was prepared by adding 16 grams of NaOH to deionized water and made up to 1000 ml. The stock solutions were stored at room temperature until ready for use. Prior to usage equal volumes of Solution A and B were mixed and incubated at 37° C. to cyclize. The cyclized solution was then added at 2 percent vol/vol concentration to the CCV fluids. The fluids were mixed thoroughly and incubated at 37° C. for 72 hours. At the end of this incubation 20 ml. of a sterile 1 molar sodium thiosulfate solution was added to insure neutralization of the BEI. Diluted and undiluted samples of the inactivated fluids were placed in susceptible tissue culture to detect any non-inactivated virus. The tissue culture was passaged three times and examined via fluoroscent antibody using specific CCV conjugate. Tests indicated complete inactivation.

EXAMPLE 3

This example illustrates an alternate inactivation procedure.

Non-frozen canine coronavirus fluids produced as described in Example 1 were inactivated with beta-propiolactone (BPL). The virus fluids at a 1 liter volume were buffered with 5 ml. of 1 normal sodium hydroxide to compensate for the pH change resulting from the acidic products released from the beta-propiolactone hydrolization. One half of one ml. of concentrated BPL was added to the fluids. The fluids were held at 4° C.±1° C. for 24 hours with periodic agitation. After which time the fluids were sampled, passaged on tissue culture, and tested via fluorescent antibody testing for any non-inactivated virus. Tests indicated complete inactivation.

EXAMPLE 4

This example illustrates adjuvanting the inactivated virus.

Adjuvant 4A, ethylene maleic anhydride, was prepared in the following manner. EMA 31 at 150 grams of Monsanto lot LC07 was dissolved in 3 liters of deionized water and heated to 85° C. The mixture was agitated until the EMA 31 was visibly dissolved. Phenol red, lot number 7715, ICN Pharmaceuticals, was added at 0.03 grams. The pH of the preparation was adjusted to 6.8 with 175 milliliters of 10 normal sodium hydroxide, Eastman Kodak Co. The adjuvant was dispensed into 6 glass screw cap bottles at 500 milliliters each and subjected steam sterilization at 15 pounds per square inch pressure and a temperature of 121 degrees centigrade for 2 hours.

Adjuvant 4B, a CSMA aqueous suspension, was prepared in the following manner. Neocryl A-640 lot RL-414 at 7.5 liters was mixed with 7.5 liters of deionized water containing 70 grams of sodium chloride, lot KMPA, Mallinckrodt. The preparation was mixed and dispensed into 30–500 milliliter glass screw top containers. These were subjected to steam sterilization at 15 pounds per square inch pressure and 121 degrees centigrade temperatures for 2 hours.

Killed canine coronavirus antigen at 25 liter was combined with 271.7 milliliters of adjuvant 4A. There was a pH shift to acid and this was adjusted with 21 milliliters of 1 normal sodium hydroxide resulting in a pH of 7.5. To the mixture 1902.6 milliliters of adjuvant 4B was added. The entire bulk vaccine was mixed and filled into 18,850 13 millimeter finish type I minivial vaccine containers for testing and evaluation.

EXAMPLE 5

This example illustrates alternative adjuvanting of the inactivated virus.

One liter of canine coronavirus fluids which were inactivated with 2 percent BEI was used in this process. The adjuvants were prepared in the following manner:

ADJUVANT 5A—Ethylene-maleic anhydride (EMA) solution was prepared in the following manner. Phosphate buffered saline (PBS) was prepared at 0.01M. in deionized water. Eight grams of sodium chloride (NaCl) per liter was added with 0.2 grams of potassium chloride (KCl), 1.15 grams of sodium phosphate dibasic ($Na_2HPO_4$) and 0.2 grams of potassium phosphate mono basic ($KH_2PO$). Sixty three hundred ml. of PBS were used in preparing the EMA. The PBS was heated to 100° C. Three hundred and fifteen grams of EMA 31 #LCO7329 (Monsanto Co, 800 N. Lindberg Blvd., St. Louis, Mo. 63166) was added and dissolved in the PBS. Phenol red at 0.05 grams was added to facilitate gross pH adjustments. Once dissolved the pH of the solution was adjusted to 6.8 with 260 ml. of 10 normal sodium hydroxide (NaOH). The solution was dispensed into 500 ml. screw cap bottles and sterilized by autoclaving at 121° C. at 15 psi for 2 hours.

ADJUVANT 5B—CSMA suspension diluted in PBS was prepared in the following manner. Five gallons of the same PBS as described above with regard to adjuvant 5A was mixed with 5 gallons of Neocryl A640 lot RC-4570 (Polyvinyl Chemical Industries, 730 Main Street, Wilmington, Mass. 01887). The suspension was thoroughly mixed and dispensed into 500 ml. screw top bottles and 12 liter jugs. These vessels were autoclaved for 3 hours at 121° C., 15 psi to sterilize.

One liter of the CCV inactivated fluids were mixed thoroughly via a magnetic mixer. Sixty ml. of adjuvant 5A was added. Immediately, 10 ml. of 1 normal NaOH was added to adjust the pH to 7.34 (as determined by an Orion pH meter). One hundred ml. of adjuvant 5B was added. The mixture was allowed to mix for 10 minutes then dispensed into aliquots for animal testing.

EXAMPLE 6

This example illustrates the effectiveness of various adjuvants with inactivated canine coronaviruses (CCV) KV.

Fifty-two dogs seronegative and susceptible to CCV were used to demonstrate the effectiveness of several adjuvant systems with a killed canine coronavirus vaccine. All test dogs were parenterally inoculated with one dose of product. A two dose vaccination regimen was used. Serum neutralizing antibody levels were determined 3 weeks post one inoculation and two weeks post a second inoculation.

| Reciprocal Geometric Mean Serum Neutralizing Antibody Levels | | | | | |
|---|---|---|---|---|---|
| Number of Test Dogs | Antigen Level | Adjuvant types used | Pre Vaccination | 3 wks. post 1st vaccination | 2 wks post 2nd vaccination |
| 11 | Minimum | EMA 31 & Neocryl A640 | <2 | 8.9 | 48 |
| 12 | Minimum | EMA 31 & Neocryl A640 | <2 | 17.8 | 30.7 |
| 5 | Full | EMA 31 & Neocryl A640 | <2 | 19 | 62 |
| 4 | Full | Neocryl A640 | <2 | 16 | 28 |
| 5 | Full | Aluminum Phosphate | <2 | 17.5 | 32 |
| 5 | Full | Aluminum Hydroxide Alhydrogel | <2 | 12.5 | 38 |
| 5 | Full | Aluminum Hydroxide Reheis | <2 | 38.2 | 57.6 |
| 5 | Full | Neocryl & Aluminum Phosphate | <2 | ≦9.9 | 53.9 |

Alhydrogel and Reheis are trade names for aluminum hydroxide.

The data indicates any number of classical adjuvant systems can be used to induce a good systemic antibody response with the CCV KV product. The data does indicate the combined adjuvant system of EMA-31 and Neocryl-A640 as being superior.

EXAMPLE 7

This example illustrates the procedure for vaccine evaluation.

This study was designed to determine the feasibility and degree of efficacy of an inactivated cornavirus vaccine. The adjuvanted product described in Example 5 was utilized for these studies. The study would also determine whether one dose or two would be required to adequately protect the canine. Ten dogs, which were tested by serum neutralization tests to be CCV seronegative, were utilized in the two-part study. Six of the dogs, numbers 214, 222, 219, 220, 212 and 213, were given a one ml. dose of vaccine administered intamuscularly. These dogs were bled on days 4, 7, 11, 14 and 21 post first vaccination to serologically monitor the response to the vaccine. Dogs 214 and 222 along with challenge controls, 244 and 245, were challenged intranasally-orally with I-171 virus (ATCC VR-809). At 5 days post challenge the four animals were euthanized and examined for evidence for coronaviral infection. Gross pathology showed a remarkable inflammation of the small intestines in the challenge controls (244 and 245). The vaccinates however, showed slight, if any, signs of inflammation. The same held true on examination of the pancreas. Samples of the brain, meninges, lungs, liver, spleen, mesentary, mesentary lymp nodes, pancreas and 10 samples at equal distance and locations in the intestines were taken from each dog for CCV detection by exfoliation fluorescent antibody. Results are presented in Table 7-1.

TABLE 7-1

CCV Dog Study
One Dose Killed Canine Coronavirus Vaccine
CCV-FA-Exfoliation Results 5 days Post Challenge
Dog # and Treatment Group

| Tissue | Vaccinates | | | Controls | | |
|---|---|---|---|---|---|---|
|  | 214 | 222 | Average | 244 | 245 | Average |
| Brain | — | — | 0 | — | — | 0 |
| Meninges | — | — | 0 | — | — | 0 |
| Lung | — | — | 0 | — | — | 0 |
| Liver | — | — | 0 | — | ½+ | ¼+ |
| Spleen | — | — | 0 | — | — | 0 |
| Mesentery | — | — | 0 | — | — | 0 |
| Mesentery Lymph Node | — | — | 0 | — | — | 0 |
| Pancreas | — | — | 0 | — | — | 0 |
| Intestine 1 | — | — | 0 | 4+ | 1+ | 2.5+ |
| Intestine 2 | — | — | 0 | 4+ | 4+ | 4+ |
| Intestine 3 | — | — | 0 | 4 | 3+ | 3.5+ |
| Intestine 4 | — | — | 0 | 2+ | 2+ | 1.5+ |
| Intestine 5 | — | ¼+ | ⅛+ | 4+ | 3+ | 3.5+ |
| Intestine 6 | — | — | 0 | 4+ | 2+ | 3.0+ |
| Intestine 7 | — | ¼+ | ⅛+ | 4+ | 3+ | 3.5+ |
| Intestine 8 | — | — | 0 | 4+ | — | 2+ |
| Intestine 9 | — | — | 0 | 2+ | — | 1+ |
| Intestine 10 | — | — | 0 | 3+ | ¼+ | 1.6+ |
| Total Intestine | 0 | ½+ | ¼+ | 35+ | 17¼+ | 52¼ |

TABLE 7-1-continued

CCV Dog Study
One Dose Killed Canine Coronavirus Vaccine
CCV-FA-Exfoliation Results 5 days Post Challenge
Dog # and Treatment Group

| Tissue | Vaccinates | | | Controls | | |
|---|---|---|---|---|---|---|
| | 214 | 222 | Average | 244 | 245 | Average |
| Kidney | — | — | 0 | — | — | 0 |

In comparing the degree of infection as evidenced by the exfoliation fluorescent antibody it was apparent that the vaccine was efficacious in reducing viral infection of the intestines. An overall fluorescent antibody (FA) average of 52 ¼+ was demonstrated in the challenge controls. The vaccinates were demonstrated to have a ¼+FA average. This indicated a 99.5 percent reduction in the vaccinates as compared to challenge controls. As shown in application Ser. No. 504,434, supra, a modified live vaccine had provided a 95 percent reduction therefore, establishing that the protection afforded by the inactivated vaccine were comparable.

Serum neutralization (SN) tests on the 14 and 21 post vaccination and 5 day post challenge bleedings were conducted. "KV" denotes "killed virus." Results are presented in Table 2.

TABLE 7-2

SN Results Post One Dose of KV CCV
and Comparison with Challenge Controls

| Animal Designation | Vaccine | SN 14 days post vaccination | 21 days post vaccination and day of challenge | 5 days post challenge |
|---|---|---|---|---|
| 214 | 1 dose KV CCV | 1:224 | 1:224 | 1:851 |
| 222 | 1 dose KV CCV | 1:34 | 1:59 | 1:224 |
| 244 | None:Challenge Control | Not Tested | <1:2 | 1:5 |
| 245 | None:Challenge Control | Not Tested | <1:2 | 1:5 |

From Table 2, it is apparent that a 1:59 SN antibody level is sufficient for protection. Both vaccinates responded with one dose of vaccine to have a sufficient serum neutralization antibody titer along with local target immunity to provide protection against infection. The challenge controls at the time of challenge serologically responded further proving that they were challenged. The vaccinates at 5 days post challenge responded at the first stages of an amnestic response.

The second dose phase of the study began 21 days post first vaccination. The four remaining dogs were given a second 1 ml. dose of the inactivated CCV vaccine, administered intramuscularly.

At two weeks post secoond vaccination the four vaccinates, 212, 213, 219 and 220 were challenged along with 2 susceptible corona control dogs, 270 and 271. The I-171 (ATCC VR-809) coronavirus was used as challenge. Five ml. per dog was administered intranasally and orally. At five days post challenge, all six dogs were euthanized and samples of the intestines, spleen, brain and meninges were taken for exfoliation fluorescent antibody testing for canine coronavirus detection. Ten samples of the intestines were taken with only individual samples of the other organs being taken. Exfoliation results are summarized in Table 7-3.

TABLE 7-3

EXFOLIATION CCV FA RESULTS POST CHALLENGE

| Dog # | Vaccine | SAMPLES | | | | | | | | | | Spleen | Brain | Meninges | Total Infectivity |
|---|---|---|---|---|---|---|---|---|---|---|---|---|---|---|---|
| | | Intestines | | | | | | | | | | | | | |
| | | 1 | 2 | 3 | 4 | 5 | 6 | 7 | 8 | 9 | 10 | | | | |
| 212 | 2 doses CCV(KV) | 0 | ¼+ | 0 | 0 | 0 | 0 | 0 | 0 | 0 | ½+ | 0 | 0 | 0 | 0.75 |
| 213 | 2 doses CCV(KV) | 0 | 0 | 0 | 0 | 0 | 0 | 0 | 0 | 0 | 0 | 0 | 0 | 0 | |
| 219 | 2 doses | 0 | 0 | 0 | 0 | 0 | 0 | 0 | 0 | 0 | 0 | 0 | 0 | 0 | |
| 220 | 2 doses CCV(KV) | 0 | 1+ | 1+ | 2+ | 0 | 0 | 0 | 0 | 0 | ¼+ | 0 | 0 | 0 | 4.25 |
| 270 | Challenge Control | 4+ | 3+ | 3+ | 2+ | ½+ | 2+ | 1+ | 4+ | 1+ | 4+ | ¼+ | 0 | ½+ | 25.125 |
| 271 | Challenge Control | 3+ | 2+ | 4+ | 1+ | 2+ | 3+ | 3+ | 2+ | 2+ | 1+ | 0 | 0 | ½+ | 23.5 |

The average for the two controls for CCV infectivity was 24.3. The average for the four vaccinates was 1.25. The overall reduction in infectivity was 94.9 percent in comparison of vaccinates to controls. It was noted that CCV viral replication in the meninges occurred in the controls. No indication of virus was seen in the meninges of the vaccinated animals after challenge. Protection against meningial infection was therefore afforded the vaccinates.

EXAMPLE 8

This example demonstrates the compatibility of CCV KV with other virus fractions.

The objective of this study was to demonstrate that the killed Canine Coronavirus vaccine can be used in combination with Canine Distemper virus, Canine Adenovirus Type 2, Canine Parainfluenza and Canine Parvovirus vaccines.

Experimental Design

1. Vaccination

Twenty-one seronegative dogs were vaccinated with a 1 ml. volume of the immunogenicity serial. Ten dogs were subcutaneously vaccinated and eleven dogs were intramuscularly vaccinated.

The twenty-one vaccinates and seven environmental controls were bled at the time of vaccination, at 21 days post vaccination at which time the vaccinates were reinoculated, at 14 days post second vaccination.

Antibody level determinations were made on all vaccinates for all five viral agents to demonstrate the level of antibody response which can be expected with the combination product [DA$_2$PC(KV)-CPV(MLV)]. The purpose of this data was to determine if antigen blockage occurs.

Antigen Compatibility (See Table 8-1)

Table 8-1 is a summary table citing the geometric mean antibody titers for each of the five fractions contained in the combination product.

The data establishes the antibody titers expected with a minimum potency KV combination serial. The data indicates all vaccinates responded to vaccination and that no antigen blockage occurred. To challenge data establishes the immunological properties of the KV CCV fraction were not interfered with by the four other virus fractions (CDV, CAV-2, CPI, CPV) which were present in the vaccine.

TABLE 8-1

| | | GEOMETRIC MEAN ANTIBODY TITERS | | | | | | | | | |
|---|---|---|---|---|---|---|---|---|---|---|---|
| | | 3 Weeks Post 1st Vaccination | | | | | 2 Weeks Post 2nd Vaccination | | | | |
| Route of Vaccination | # Dogs | CDV | CAV2 | CPI | CCV | CPV | CDV | CAV2 | CPI | CCV | CPV |
| Subcu | 10 | ≦1.8 | 1006.9 | 54.3 | ≦7.01 | 4111.5 | 260.6 | ≧109.4 | 153.8 | 75.7 | 6237.3 |
| IM | 11 | ≦6.7 | 538.2 | 42.6 | 8.9 | 1150.6 | 670.4 | ≧1243.2 | 259.2 | 48. | 6270.1 |
| Overall | 21 | ≦3.58 | 752.2 | 47.7 | ≦7.9 | 2110.0 | 427.5 | ≧1168.5 | 202.8 | 59.7 | 6254.5 |

EXAMPLE 9

This example illustrates canine coronavirus cross neutralization between five various isolates.

Studies were conducted to determine the cross neutralization relationships (serum neutralization of virus) between various isolates of canine coronavirus. Specific antiserum to each individual isolate was prepared in susceptible dogs. Serum neutralization (SN) tests with the various isolates at constant levels or titers were run against twofold dilutions of the specific antisera. In other words the antibody induced in the dogs by a specific isolate was evaluated as to the antibody's ability to neutralize various other virus isolates as well as the identical virus isolate used to induce the antibody. A virus isolate which induced antibody which will neutralize the most virus isolates is the best vaccine virus candidate. Results of those tests are depicted in the following table. The specific antisera are presented vertically against the various isolates listed horizontally. The reciprocal SN level is expressed.

| Antisera produced by indicated CCV | Antibody level against the virus inducing antibody formation | Antibody levels against other viruses | | | | |
|---|---|---|---|---|---|---|
| | | I-171 | K-378 | S-378 | A76-5 | ATCC VR 2068 |
| I 171 | 89 | — | 128 | 89 | 20 | 45 |
| K-378 | 45 | 22 | — | 89 | 3 | 40 |
| S-378 | 178 | 178 | 148 | — | 6 | 37 |
| A76-5 | 11 | 45 | 32 | 64 | — | 50 |
| ATCC No. VR 2068 | 45 | 64 | 128 | 54 | 25 | — |

The data was analyzed from the standpoint of the antibody which would neutralize all five viruses. The antibody induced by the ATCC No. VR2068 virus isolate neutralized the other four viruses to a significant degree.

The A76-5 antiserum and virus proved to be the least cross reactive of the five isolates tested. The ATCC VR 2068 proved to have a significant level of cross reactivity with this virus isolate.

The data also indicates that there are no major serological differences among these five canine coronaviruses. The I-171 and ATCC VR 2068 viruses are indicated as the best choices for vaccine strains; however due to the cross neutralization between all the isolates any of the canine coronaviruses could be used as an antigen.

EXAMPLE 10

This example illustrates Vaccine Efficacy.

Twenty-eight dogs seronegative to CDV, $CAV_2$, CPI, CCV and CPV were used as vaccinates and sentinel controls. Twenty-one dogs were used as vaccinates and seven dogs were used as environmental or sentinel controls. The seven environmental controls along with three additional dogs seronegative to CCV were used as challenge control dogs. Thirty-one dogs were used for the entire study.

Twenty-one seronegative dogs were vaccinated with a 1 ml. volume of the immunogencity serial. Ten dogs were subcutaneously vaccinated and eleven dogs were intramuscularly vaccinated. The twenty-one vaccinates and seven environmental controls were bled at the time of vaccination, at 21 days post vaccination at which time the vaccinates were reinoculated, at 14 days post second vaccination and at 28 days post second vaccination which was also the day of challenge.

Antibody level determinations were made on all environmental control for all 5 viral agents to demonstrate that no exposure to extraneous virus occurred during the course of the study. Pre-challenge antibody level determinations were made to demonstrate the susceptibility of the challenge controls dogs to CCV.

The 21 vaccinates and 10 control dogs were bled, anesthetized and challenged with the CCV I-171 challenge virus identity. Each dog received 2 ml. per naris and 3 ml. orally or 5 ml. of challenge per dog. White blood cell-lymphocyte counts were performed 2 days prior to challenge and 6 to 7 days following challenge.

Five dogs vaccinated by the subcutaneous route, five dogs vaccinated by the intramuscular route and five challenge control dogs were euthanized 6 days following challenge. On day 7 post challenge five dogs vaccinated by the subcutaneous route, six dogs vaccinated by the intramuscular route and five challenge control dogs were euthanized.

The small intestine was removed and 10–13 inch sections from each dog was used for sampling. The ten sections were taken from the same areas in each dog. The first section (sample 1) was taken just below the stomach and the last section (sample 10) was obtained just above the small intestine-large intestine junction. Each section was scraped and the intestinal samples suspended in PBS. The tubes containing the cell suspension were grossly observed for appearance. Cell samples from each tube were placed on sides which were air dried, acetone fixed and stained with canine coronavirus antibody conjugate. These slides were then evaluated to determine the degree of viral infection which existed in the cells.

RESULTS AND DISCUSSION

A. White Blood Cell Counts Post Challenge

A white blood cell count reduction of greater than 45% from the baseline was used for purposes of evaluating this study.

Vaccinates

Six observations of WBC drops greater than 45% from baseline were recorded out of the 65 WBC counts performed on the dogs inoculated subcutaneously. The WBC count index number (6 divided by 65) was 0.092.

Three observations of WBC drops greater than 45% from baseline were recorded out of the 72 WBC counts performed on the dogs inoculated intramuscularly. The WBC count index number (3 divided by 72) was 0.042.

Controls

Twenty observations of WBC drops greater than 45% from baseline were recorded out of the 65 WBC counts performed on the challenge control dogs. The WBC count index number (20 divided by 65) was 0.308 for the challenge controls. Another way of expressing this data is that 30.8% of the WBC counts performed on the challenge control dogs were 45% below the pre-challenge baseline counts.

Discussion

The present prevention of WBC count decreases below 45% when comparing vaccinates to controls is 79.6%. The majority of the WBC decreases occured on days 2 and 3. Table 10A compares the WBC drops of vaccinates versus controls on a daily basis.

TABLE 10A

| Days Post Challenge | Percentage of dogs showing a WBC drop of 45% or greater below baseline | |
|---|---|---|
| | Controls | Vaccinates |
| 1 | 0 | 0 |
| 2 | 20 | 28.6 |
| 3 | 70 | 9.5 |
| 4 | 50 | 0 |
| 5 | 20 | 0 |
| 6 | 20 | 4.8 |
| 7 | 40 | 0 |

The vaccine therefore provided significant protection to the vaccinates in the prevention of drops in WBC counts

B. Lymphocyte Cell Count Drops Post Challenge

A lymphocyte cell count reduction of greater than 50% from the baseline was used for purposes of evaluating this study.

Vaccinates

Six observations of lymphocyte drops greater than 50% from baseline were recorded out of 65 lymphocyte counts performed on the challenge control dogs. The lymphocyte count index number (16 divided by 65) was 0.246 for the control dogs.

Three observations of lymphocyte drops greater than 50% from baseline were recorded out of the 72 lymphocyte counts performed on the dogs inoculated intramuscularly. The lymphocyte count index number (3 divided by 72) was 0.042 for this group.

Controls

Sixteen observations of lymphocyte drops greater than 50% from baseline were recorded out of 65 lymphocyte counts performed on the challenge control dogs. The lymphocyte count index number (16 divided by 65) was 0.246 for the control dogs.

The lymphocyte dogs occurred most frequently on day 4 post challenge with 7 of 10 dogs (70%) demonstrating a drop in lymphocytes. Two other days showing a high frequency of lymphocyte drops post challenge were day 3 with 5 of 10 dogs (50%) and day 2 with 3 of 10 (30%).

Discussion

The present prevention of lymphocyte count decreases below 50% when comparing vaccinates to controls was 73.2%.

The majority of lymphocyte decreases occurred on days 2, 3 and 4 post challenge. Table 10B compares the lymphocyte drops of vaccinates versus controls on days 2, 3 and 4 post challenge.

TABLE 10B

| Days Post Challenge | Percentage of dogs showing lymphocyte drop of 50% or greater below baseline | |
|---|---|---|
| | Controls | Vaccinates |
| 2 | 9.5 | 30.0 |
| 3 | 19.0 | 50.0 |
| 4 | 4.8 | 70.0 |

The data demonstrates that the killed CCV vaccine provided significant protection to the vaccinates in the prevention of drops in lymphocytes following challenge.

C. Intestinal Infection with Canine Coronavirus Post Challenge

Vaccinates

The 210 intestinal samples were examined for the presence of CCV virus by the fluorescent antibody staining technique. Five of the 210 samples (2.4%) were positive for virus. The degree of infection did not exceed an $\frac{1}{8}+$.

No fluorescence typical of CCV virus was observed in the meninges of any of the vaccinates.

The number of samples positive per degree of infection $(4+-\frac{1}{8}+)$ were totaled and the Total FA+ for each dog determined. The infective index for each dog was calculated by the following method.

A group infective index was obtained by totaling the individual dogs infective index and dividing by the total number of dogs in each group.

The infective index for the subcutaneously vaccinated dogs was 0.0025 while the infective index for the intramuscularly vaccinated dogs was 0.0034.

The infective index for the vaccinates examined on day 6 versus those examined on day 7 did not vary significantly.

Controls

The 100 intestinal samples were examined for the presence of CCV virus by the fluorescent antibody staining technique. Eighty-one (81) of the 100 samples (81%) were positive for virus. The degree of infection ranged from a 4+ (highly infected samples) to negative. All ten challenge control dogs (100%) demonstrated CCV infection of the intestinal tract.

Three of the 10 challenge control dogs (30%) demonstrated fluorescence typical of CCV in their meninges.

The number of samples positive per degree of infection (4+ to ⅛+) were tallied. The same calculation methods used above were used for this data.

The infective index for the challenge control dogs is 1.594. The infective index for the challenge control dogs examined on day 6 versus those examined on day 7 did vary to some degree. Ninety percent of the samples of the control dogs examined on day 6 were positive while seventy-two percent of the samples of the control dogs examined on day 7 were positive. The degree of infection was 36.5% less on day 7 versus day 6. All of the control dogs were infected with CCV.

Discussion

A comparison was made of vaccinates and controls in relation to the severity and incidence of intestinal infection. The data was also broken down between the 6 day and 7 day post observation periods. The results indicate the degree of protection provided is not dependent upon the route of vaccination.

The vaccine reduced the degree of infection in the vaccinates by at least 99.7%. The data based on the incidence of positive samples per test group irregardless of the degree of infection indicates the vaccine reduced the degree of infection in the vaccinates by at least 95.6%. The data obtained from the samples observed on day 6 and 7 post challenge shows 98.1% reduction in intestinal infection as measured by severity and incidence was provided by the vaccine. A 97% reduction in intestinal infection as measured by incidence was provided by the vaccine. The test parameters of temperature response, white blood cell response and lymphocyte response for both vaccinates and controls post challenge were summarized. It is pointed out that CCV virus was observed in the meninges of 30% of the controls whereas no CCV virus was observed in any of the vaccinate's meninges.

D. Serological Data

Environmental Controls

Antibody level determinations on the seven environmental controls indicated no exposure to extraneous CDV, CAV-2, CPI or CPV virus occurred during the course of the experiment. These antibody level tests were conducted on blood specimens drawn five weeks post 1st vaccination which also represents the 2 weeks post second vaccination time period.

Pre and Post Vaccination Antibody Levels to Canine Coronavirus

Vaccinates

The antibody titers of the vaccinates at the time of vaccination, at 3 weeks post 1st vaccination, 2 weeks post second vaccination, 4 weeks post second vaccination and 6 or 7 days post challenge indicate all vaccinates were seronegative prior to vaccination. The data indicates 20 of 21 vaccinates (95.2%) serologically responded to the first vaccination. The geometric mean titer was 1:7.9. The two weeks post second vaccination geometric mean titer increased 7.6 fold to a 1:59.7 titer. All vaccinates had SN titers of greater than or equal to a 1:9 SN titer. The four week post second vaccination geometric mean titer increased another 1.57 fold to a 1:93.9 titer. The lowest antibody titer recorded at the 4 week post second vaccination period was 1:34. The subcutaneous route of vaccination appeared to elicit a somewhat higher antibody titer than did the intramuscular route of vaccination.

The post challenge SN antibody levels indicate a lower antibody level was observed in the vaccinates following challenge. The 5 and 6 day post challenge bleeding time is probably too early for amnesis to occur. It may be that the challenge virus-antibody interaction could account for the lower SN responses observed.

Controls

Seven of the ten control dogs served as environmental controls as well as challenge control dogs. The dogs were seronegative at the time of challenge thus proving no environmental exposure to live CCV virus occured during the study. This also proved their susceptibility to the challenge virus.

The 6 and 7 day post challenge antibody levels remained low. This is not unexpected. A measurable antibody response to parenteral CCV inoculation is 6–9 days. The FA observations of intestinal tract samples indicate the virus was present in the dogs but seroconversion had not been accomplished in a 7 day interval between challenge and bleeding prior to euthanizing of the dogs.

The foregoing results demonstrates the satisfactory immunogenicity of a killed Canine Coronavirus (CCV) vaccine.

What is claimed is:

1. A vaccine composition comprising inactivated canine coronavirus having a pre-inactivation titer of at least 10,000 canine coronavirus particles per milliliter and a veterinary pharmaceutically acceptable carrier therefor.

2. A vaccine composition as defined in claim 1 further comprising an adjuvant.

3. A vaccine composition according to claim 1 further comprising an adjuvant selected from the group consisting of ethylene maleic anhydride and a copolymer of styrene with a mixture of acrylic acid and methacrylic acid.

4. An vaccine composition as defined in claim 1 having a pre-inactivation titer of at least 5.0 logs of canine coronavirus particles per dose.

5. A vaccine composition according to claim 1 in parenteral injection form.

6. A vaccine composition according to claim 1 which further comprises an effective amount of at least one other canine vaccine in combination therewith.

7. A vaccine composition which comprises an amount of inactivated canine coronavirus strain ATCC VR-2068 sufficient to be effective against canine coronavirus in combination with a carrier suitable for dogs.

8. A vaccine composition comprising inactivated canine coronavirus present in an amount of about 10,000 to 10,000,000 virus particles per dose as measured by the $FAID_{50}$ method, an adjuvant selected from the group consisting of ethylene maleic anhydride and a copolymer of styrene with a mixture of acrylic acid and methacrylic acid, and a non-toxic pharmaceutically acceptable carrier.

9. The vaccine composition of claim 8 further comprising at least one additional vaccine selected from the group consisting of canine distemper virus vaccine, canine parainfluenza virus vaccine, canine adenovirus I vaccine, canine adenovirus II vaccine, and canine parvovirus vaccine.

10. The vaccine composition of claim 8 where the canine coronavirus is ATCC No. VR-2068.

11. A canine coronavirus vaccine composition comprising an amount of inactivated canine coronavirus which is equivalent to a virus titer of from about 4 to 7 logs $FAID_{50}$ per milliliter, in an aqueous solution having a pH between about 6.8 and 7.8.

12. The method of protecting dogs against virulent canine coronavirus comprising inoculating a dog with inactivated canine coronavirus vaccine prepared by a process which comprises the steps of growing a strain of canine coronavirus in a non-oncogenic cell culture and then inactivating the virus.

13. The method of claim 12 wherein said cell culture comprises kidney cells.

14. The method of protecting dogs from meningeal infection due to coronavirus which comprises parenterally inoculating the animal with a killed, adjuvanted coronavirus vaccine.

15. The process of making a canine coronaviruus vaccine comprising the steps of:

a. inoculating a suspension of mammalian tissue cell cultures with canine coronavirus;
b. harvesting said cells after about 24 to 96 hours; and
c. collecting the propagated virus from the harvested cells;
d. inactivating the propagated virus; and
e. adding an adjuvant to the inactivated composition.

16. The process of claim 15 wherein said tissue cell culture is cultivated into a confluent monolayer prior to inoculation with said virus.

17. The process of claim 15 wherein said tissue cell culture is cultivated into a confluent monolayer within 24 hours after inoculation.

18. The process of claim 15 where the inactivation is accomplished by adding to the cell culture an inactivating agent selected from the group consisting of binary ethyleneimine, acetyl ethyleneimine, beta-propriolactone, formalin and phenol.

19. The process as defined in claim 15 where the cell culture consists of Crandall Feline Kidney Cells.

* * * * *